(12) United States Patent
Eagleman et al.

(10) Patent No.: US 9,095,295 B2
(45) Date of Patent: Aug. 4, 2015

(54) DEVICE AND METHOD FOR MEASURING INFORMATION PROCESSING SPEED OF THE BRAIN

(75) Inventors: David M. Eagleman, Houston, TX (US); Matthew P. Fiesta, Houston, TX (US); Chess A. Stetson, Pasadena, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1043 days.

(21) Appl. No.: 12/439,232

(22) PCT Filed: Sep. 4, 2007

(86) PCT No.: PCT/US2007/077529
§ 371 (c)(1),
(2), (4) Date: Feb. 27, 2009

(87) PCT Pub. No.: WO2008/091399
PCT Pub. Date: Jul. 31, 2008

(65) Prior Publication Data
US 2009/0270758 A1 Oct. 29, 2009

Related U.S. Application Data

(60) Provisional application No. 60/824,362, filed on Sep. 1, 2006.

(51) Int. Cl.
*A61B 13/00* (2006.01)
*A61B 3/02* (2006.01)
*A61B 5/16* (2006.01)
*A61B 3/032* (2006.01)

(52) U.S. Cl.
CPC ............. *A61B 5/161* (2013.01); *A61B 3/022* (2013.01); *A61B 3/032* (2013.01); *A61B 5/16* (2013.01); *A61B 5/162* (2013.01); *A61B 5/165* (2013.01)

(58) Field of Classification Search
CPC .......... A61B 3/022; A61B 3/032; A61B 5/16; A61B 5/161; A61B 5/162
USPC ......... 600/587, 558, 523, 522, 443, 383, 405, 600/400, 356, 318, 162, 24; 345/168, 133, 345/657, 104, 87, 33, 60, 24, 64; 351/222
See application file for complete search history.

(56) References Cited

U.S. PATENT DOCUMENTS 4,861,156 A * 8/1989 Terry ........................... 351/243
5,289,389 A 2/1994 Keller
(Continued)

OTHER PUBLICATIONS

International Search Report dated Jul. 22, 2008 for International Application No. PCMS2007/077529, 4 pages.

*Primary Examiner* — Devin Henson
(74) *Attorney, Agent, or Firm* — Conley Rose, P.C.

(57) ABSTRACT

A device is disclosed which comprises a display adapted to display a sequence of rapidly alternating images, and a keypad electrically coupled to the display, for entering a perceived sequence by a user. The device is configured to compare a perceived sequence input by the user to the displayed sequence, and to measure the speed of visual perception of the user. Also disclosed are methods of visually, non-invasively assessing an individual's speed of visual perception (visual window of integration), or detecting any changes that have occurred in the individual's speed of visual perception.

18 Claims, 8 Drawing Sheets

(56) References Cited

U.S. PATENT DOCUMENTS

| | | | |
|---|---|---|---|
| 5,694,199 A * | 12/1997 | Rodriguez | 351/223 |
| 6,102,870 A * | 8/2000 | Edwards | 600/558 |
| 6,208,348 B1 * | 3/2001 | Kaye | 345/419 |
| 6,226,997 B1 * | 5/2001 | Vago | 62/130 |
| 6,231,187 B1 * | 5/2001 | Munoz et al. | 600/558 |
| 6,352,517 B1 * | 3/2002 | Flock et al. | 600/595 |
| 6,579,247 B1 * | 6/2003 | Abramovitch et al. | 600/587 |
| 6,677,969 B1 * | 1/2004 | Hongo | 715/863 |
| 6,755,529 B2 * | 6/2004 | Stewart et al. | 351/243 |
| 7,004,912 B2 * | 2/2006 | Polat | 600/558 |
| 7,163,513 B2 * | 1/2007 | Darby et al. | 600/558 |
| 7,175,598 B2 * | 2/2007 | Yoneyama | 600/443 |
| 7,331,929 B2 * | 2/2008 | Morita et al. | 600/558 |
| 7,347,694 B2 * | 3/2008 | Berger et al. | 434/258 |
| 7,367,671 B2 * | 5/2008 | Sabel | 351/203 |
| 7,760,231 B2 * | 7/2010 | Sayre | 348/189 |
| 7,983,456 B2 * | 7/2011 | Rao et al. | 600/443 |
| 2002/0099305 A1 * | 7/2002 | Fukushima et al. | 600/558 |
| 2002/0198577 A1 * | 12/2002 | Jaillet | 607/88 |
| 2003/0032894 A1 * | 2/2003 | Hu et al. | 600/558 |
| 2003/0158497 A1 * | 8/2003 | Graham et al. | 600/558 |
| 2003/0223038 A1 * | 12/2003 | Alster et al. | 351/211 |
| 2005/0065452 A1 * | 3/2005 | Thompson | 600/558 |
| 2005/0192513 A1 * | 9/2005 | Darby et al. | 600/558 |
| 2005/0195216 A1 * | 9/2005 | Kramer et al. | 345/619 |
| 2005/0213040 A1 * | 9/2005 | Gross et al. | 351/243 |
| 2006/0126093 A1 * | 6/2006 | Fedorovskaya et al. | 358/1.14 |
| 2007/0003136 A1 * | 1/2007 | Shimbaru | 382/167 |
| 2007/0027406 A1 | 2/2007 | LaPlaca et al. | |
| 2007/0066916 A1 * | 3/2007 | Lemos | 600/558 |
| 2007/0076168 A1 * | 4/2007 | Ellenbogen | 351/200 |
| 2007/0179568 A1 * | 8/2007 | Nycz et al. | 607/60 |
| 2010/0112048 A1 * | 5/2010 | Fotuhi | 424/463 |

* cited by examiner

DEVICE AND METHOD FOR MEASURING INFORMATION PROCESSING SPEED OF THE BRAIN

CROSS-REFERENCE TO RELATED APPLICATIONS

The present application claims priority under 35 U.S.C. §365 to International Patent Application No. PCT/US2007/77529 filed on Sep. 4, 2007, which claims the benefit of U.S. Provisional Patent Application No. 60/824,362 filed Sep. 1, 2006. The disclosures of those applications are hereby incorporated herein by reference.

STATEMENT REGARDING FEDERALLY SPONSORED RESEARCH OR DEVELOPMENT

Not applicable.

BACKGROUND

1. Field of Technology

The present invention generally relates to devices and methods for assessing the status of an individual's physical and/or mental performance, particularly as affected by such factors as disease, sleep deprivation, fatigue, excessive stress, alcohol or drugs. Still more particularly, the invention relates to such methods and devices which measure the speed of human visual perception.

2. Description of Related Art

Although medicine utilizes many measures of spatial vision, such as eye charts and perimetry, there are few ways to measure the temporal aspect of vision, i.e., the brain's speed of information processing. It is known that the visual brain collects information over windows of time (known as windows of integration). If two or more stimuli arrive within a single window of integration (usually less than 100 msec), they will be perceived as a single stimulus. For example, a child's toy known as a thaumatrope may have, for example, a picture of a bird on one side of a disc and a picture of a cage on the other. When the disc is wound up and spun quickly, so that both sides are seen in rapid alternation, the bird appears to be inside the cage. The two stimuli are alternating so rapidly that the visual system cannot distinguish them; they are seen as though they are simultaneously present. A good deal of data has been collected which shows that successive visual stimuli need to be presented within a small window of time (typically less than 100 msec) for the images to perceptually overlap.[7] In other words, the visual brain collects information over windows of time. Under various circumstances, the duration of these windows can change.

Traditionally, the only methodologies for measuring the brain's speed of information processing use a flickering light. When the frequency of a flickering light is increased, the perception of flicker disappears at some point. The point where flickering perceptually fuses into steady light is called the "critical flicker fusion threshold" (CFFT). Flicker fusion measurements in medicine have been used for over a century[48] for early diagnosis as well as for measurement of drug efficacy in the pharmaceutical industry.

The neurophysiology literature indicates that temporal measures involving flicker reflect something about central nervous system function. A number of studies point to CFFT being a reliable indicator of disease (such as Down's syndrome,[33] Alzheimer's disease, and generalized cortical damage) as well as a measure of the effects of psychopharmaceuticals. Patients with dyslexia, an inability to read due to cortical dysfunction, have been reported to have impaired flicker detection.[15] Flickering light is able to initiate neuronal activity in various parts of the visual system, from the retina to the brain cortex. It is clear from decades of study of disease, lesion and pharmacological agents that that the CFFT measurement relates to central nervous system (CNS) function rather than merely relating to the eyes or the optic pathways to the cortex. The central nature of flicker perception is supported by evidence that CFFT values are higher when measured with binocular vision rather than monocular vision[53,54] and that exposure of only one eye to flicker alters the threshold sensitivity of the other eye.[52] There is general agreement in the literature that CFFT is sensitive to the sedative and/or stimulant effect of CNS drugs.[52,49,26,40] There is not, however, general agreement about what it measures: CNS sedation and arousal, CNS integration, psychomotor performance, information processing capacity and/or CNS impairment.[12]

Measurements of CFFT have been used for the evaluation of psychoactive drugs,[12] and are thought by some to be the most reliable method for measuring the effects of psychoactive drugs and central depressants.[31] Detailed reviews of the application of CFFT in psychopharmacology have been published.[52,49,25,26,30,21] In general, CFFT has been shown to distinguish between drugs, and even different dosages of the same drug, where other clinical rating scales are unable to do so. Some of the drugs in which CFFT has been used to assess their effects include anxiolytics,[25,26,41,11,13,12] such as benzodiazepines, for which a reduction in threshold frequency has been observed because of their sedative effects. The measurement of CFFT is considered by some to be the most reliable technique available to assess a central depressant effect.[31]

Another class of drugs in which CFFT has been used are the antidepressants. There are reports that CFFT is lower in elderly depressed patients compared with non-depressed elderly subjects.[44] Further, the CFFT reportedly increases following treatment with anti-depressants.[45] Tricyclic antidepressants can be grouped according to their sedative properties and effects of the CFFT.[27,43] The general finding is that the tricyclics cause a greater reduction of threshold frequency compared to selective serotonin reuptake inhibitors (SSRIs).[24] New antidepressants have also been distinguished in this way.[50,26]

Still other types of prescribed medications have been reported in the literature to reduce CFFT, including beta-blockers,[17] some cough suppressants,[16] some antihistamines,[51] anticonvulsants, and some antipsychotic drugs.[40] Of the socially used drugs, alcohol is said to reduce CFFT,[28] and nicotine is said to increase CFFT.[46] The effect of caffeine remains equivocal.[35]

Although it is still an open question whether there exists a good method for early detection of Alzheimer's disease before memory disturbance is apparent, CFFT has been suggested as one approach with potential advantages over other measures used for screening purposes.[12] For diagnosing the onset of Alzheimer's disease, current methods of cognitive testing for dementia generally come too late. Neuroimaging is not practical for screening on a large scale, and currently available biochemical tests tend to identify Alzheimer's disease too late after onset. CFFT has been proposed as a non-invasive, easy to use and inexpensive means of screening people at high risk of developing Alzheimer's disease.

There have also been a number of investigations as to whether temporal measure is a signature of fatigue or arousal.[38,19,21-23] A significant correlation between CFFT and self-rated alertness scores have been reported, and others have found that CFFT was significantly correlated with cortical alpha activity (a measure of arousal) measured by EEG. The correlation coefficients were relatively low, however, suggesting that CFFT is not simply a measure of sedation/arousal[39] and it has been noted in the literature that the exact meaning of CFFT threshold changes is difficult to specify. CNS arousal/sedation is not a simple concept and may be the final outcome of many different processes. Furthermore, CNS drugs have many effects on brain function other than sedation/arousal, as illustrated by the effect of antidepressants. Although sedative antidepressants reportedly cause a reduction in CFFT scores in the early phase of treatment, CFFT scores increase as the depression resolves.[45] This cannot be explained simply as "arousal," since improvement is associated with many changes, including increased appetite, increased speed of thought processes, reduced psychomotor retardation, enhanced noradrenalin (NA) and serotonin/5-hydroxytryptamine (5-HT) functioning, restoration of biological rhythms and an ability to experience pleasure, to name just a few. Thus, although CFFT appears to reflect some aspect of CNS sedation/arousal, this concept is poorly defined and is the final outcome of a great many different processes.[12]

Many studies have shown that the CFFT has high test/retest reliability.[8,36,32,38,55,48,26,31] Thus, the CFFT is generally very stable for an individual subject, although it decreases slightly with increasing age. There is a slight degree of individual variability between subjects. Slight correlations have been reported between CFFT and eye color[49] as well as intelligence,[37] however, those correlations were low. The traditional method of flickering light has found that CFFT is affected by pupil size, being highest for large pupil sizes, which could be important if subjects are taking any medication that affects pupillary diameter. The stability of CFFTs allow changes in this measure to be potentially useful in diagnosis and psychopharmacology.

Existing data on CFFT indicates that long exposures to flickering light can alter the threshold, and CFFT is highest at the periphery of the retina and decreases towards the fovea. It is also known that CFFT increases with stimulus luminance and decreases with increasing luminance of the area surrounding the stimulus. CFFT also increases with the stimulus size.

Despite the increased knowledge that has been gained in recent years about the factors influencing CFFT, the basic measuring methodology has remained essentially unchanged. Available methods for measuring the CFFT typically require tens of minutes to conduct, necessitate training and expertise in administering the test, and are susceptible to falsification by the test subject.

Currently there are three primary methodologies for measuring CFFT. The first method is the "method of just noticeable differences." According to this method the administrator of the test incrementally increases the frequency of a flickering light as a series of small steps. As the frequency increases, the flickering becomes more difficult to perceive and at some point fuses into an apparently solid light. The step at which this occurs is termed the "ascending threshold." Then the test administrator does the same thing in reverse, starting from a high frequency and lowering it until the light appears to flicker again. This determines the "descending threshold" of the subject. There are no rigid guidelines regarding how many ascending and descending runs should be measured. In some tests a sufficient number of trials are performed until "the data seem stable,"[14] which usually means averaging three or four ascending and descending thresholds.[34,29] Conducting a CFFT test according to this method typically takes about 5 minutes.

In a second type of CFFT testing referred to as "the method of constant stimuli," the test administrator chooses several flicker frequency stimulus values equally spaced over a range from rarely detected (well below the subject's perception threshold) to a flicker frequency that is nearly always detected by the subject (i.e., well above the threshold). These stimuli are then presented in random order. On each trial, the subject reports whether the stimulus was flickering (Yes/No response). The threshold is defined as the flicker frequency where subjects report flickering on 50% of the trials. This approach, while more exact than the first method, requires many trials, most of which are wasted because they are at the extremes of the testing range. This type of test takes up to ten times longer than the first method, making it generally unsuitable for use in clinical settings.

A similar third CFFT testing method is the "forced choice method," in which the subject is presented with two stimuli, one steady and one flickering. The subject is forced to choose which is flickering. Again, this test requires a considerable number of trials to achieve the threshold, and thus many tens of minutes to administer.

There has been no clear evidence whether extreme fatigue, the kind that will cause drivers to crash vehicles, for example, has a clear temporal signature. Medical residents, pilots, soldiers, truck drivers and others frequently work long shifts which lead to sleep-deprivation. Excessive sleep deprivation leads to poor decision making which in turn may result in avoidable accidents[3]. Today, the available methods for assessing fitness for duty (FFD) measure brain activity using electroencephalography[4,5] or ocular measures that require using eye trackers.[6] As a practical matter, these methods have limited usefulness because they require expensive equipment, large time windows for testing, and are generally not well received by subjects.[4] Other existing techniques utilize sensitive ocular measures, such as saccade velocity and speed of pupillary constriction to light.[4] Such techniques are also impractical in most situations because they require expensive and sensitive equipment such as eye trackers. Eye trackers are not only expensive, but they also require a calibration period during which a subject is required to sit still with his head on a chin rest or bite bar. Still other techniques aimed at assessing fitness for duty utilize reaction time as a measure. For example, a picture appears on a screen, and a subject has to make a motor reaction to it (e.g., touch the screen) as quickly as possible. Such techniques are useful but somewhat cumbersome because they require equipment that will measure the speed and location of the touch. There is continuing interest in development of indicators of physical or mental impairment arising from drug effects, fatigue, stress, neurological disease and other conditions that impact central nervous system function.

BRIEF SUMMARY

In accordance with certain embodiments of the invention, an automated method is provided for visually and non-invasively measuring the speed of human visual perception, specifically, the size of the window of integration, in which subjects will see alternately presented stimuli as though they were presented simultaneously. In some embodiments a portable device and the associated algorithm are provided that together yield a rapid measure of changes from the normal speed of perception. This is a potentially a highly informative measurement for determining operator changes due to fatigue, excessive stress, alcohol, drugs, and other conditions.

In accordance with certain embodiments of the invention, a device is provided which comprises a visual display configured to display at least one sequence of alternating positive and negative images; a keypad for entering a perceived sequence by a user; and a microprocessor operatively coupled to said keypad and display. The microprocessor is configured for presenting said alternating images at a predetermined alternating rate or set of alternating rates, and the microprocessor is configured for comparing said perceived sequence entered by the user to said at least one displayed sequence, and determining a threshold value corresponding to the speed of visual perception of the user. In some embodiments, the visual display comprises a cathode-ray-tube (CRT) monitor, a plasma screen, a liquid crystal display (LCD), or a group of light emitting diode (LED) arrays. For the purposes of this disclosure, the terms "processor," "microprocessor," "central processing unit" ("CPU") and "microcontroller" are interchangeable, where the context allows.

In some embodiments, the device is configured to display at least one said sequence at an alternation rate specific to a threshold of the user. In some embodiments, the alternation rate specific to the threshold of the user is preprogrammed in the microprocessor. In some embodiments, the device is configured to display said alternating images at an alternation rate specific to the user when a user-specific code is entered using the keypad. In some embodiments, the device is configured to display each of the sequences again at different alternation rates, if the perceived sequence entered by the user does not match a displayed sequence. In some embodiments, the device is configured to repeatedly display the at least one sequence of rapidly alternating positive and negative images at different alternation rates until the perceived sequence entered by the user matches a displayed sequence at a final alternation rate. In some embodiments, the device is a portable device configured to be hand held or worn on the human body.

In certain embodiments, any above-described device further comprises an indicator that is activatable if the perceived sequence entered by the user does not match a predetermined displayed sequence. In certain embodiments, any above-described device further comprises an indicator on the device that is activatable if the perceived sequence entered by the user matches a predetermined displayed sequence.

In certain embodiments, a device is configured for producing a report comprising said threshold value. In some embodiments, the visual display comprises a temporal eye chart comprising a vertically arrayed series of different alternating sequences in which the rate of alternation of each succeeding sequence in the series increases from top to bottom in the stack.

Also provided in accordance with certain embodiments of the invention is a method of assessing speed of information processing in an individual. The method comprises providing a above-described device; displaying on said visual display said alternating images at a predetermined alternating rate or set of alternating rates; observing said alternating images by said individual; entering on said keypad at least one sequence perceived by said individual from said visual display; and obtaining from said device a threshold value corresponding to the speed of visual perception of the individual.

In some embodiments, the microprocessor contains a predetermined baseline threshold value, or set of threshold values, indicative of a baseline speed of visual perception, and said method further comprises obtaining from said device a determination of any change in the individual's speed of visual perception relative to said baseline. In some embodiments, the individual being tested is a person at risk of developing Alzheimer's disease.

In some embodiments, the method comprises providing a predetermined baseline measurement or set of measurements indicative of a baseline speed of visual perception of said individual or of a control under a first condition or set of conditions; measuring the speed of visual perception of said individual under a second condition or set of conditions, to provide a second measurement or sets of measurement; and comparing said second measurements or sets of measurements with said predetermined baseline measurement or set of measurements to detect a difference in the individual's speed of visual perception under said second condition or set of conditions relative to said predetermined baseline measurement, wherein a decrease in the individual's speed of visual perception under the second condition or set of conditions indicates diminished performance ability of said individual. In some embodiments, performance ability includes the fitness of the individual for performing a predetermined duty or task, and may include such factors as decision making ability, manual dexterity and mental acuity.

In some embodiments, the second condition or set of conditions includes a condition of stress in the individual. For example, the stress may include one or more of fatigue, sleep deprivation, drug use, alcohol use, hypoxia, elevated adrenaline level, and emotional stress.

In accordance with still another embodiment of the invention, a computer-readable medium (CRM) is provided which comprises software that, when executed by a processor, causes the processor to: show on a visual display at least one sequence of alternating positive and negative images at respective predetermined alternating rates; receive from a keypad a perceived sequence entered by a user; comparing said perceived at least one sequence entered by the user to said at least one displayed sequence; and determining a threshold value corresponding to the speed of visual perception of the user. These and other embodiments, features and advantages will be apparent with reference to the following description and drawings.

DETAILED DESCRIPTION OF PREFERRED EMBODIMENTS

Although vision scientists are generally aware that the visual system has a temporal window of integration, this is believed to be the first disclosure of the use of this temporal window of integration in service of testing devices.

Example 1

Perceptual Chronometer

To rapidly measure fitness for duty (FFD), the basic principles of the human visual system were leveraged to build an apparatus (termed a "perceptual chronometer") that can be used to quickly and efficiently test fatigue. In the preferred embodiment which is described in more detail below, the apparatus is configured as a light, portable device. The recorded data is immediately available so that those unfit for duty may be temporarily relieved. In contrast to measuring physiological markers (such as EEG or papillary response times), the present device and method applies recent discoveries about human time perception[1,2].

Assessing Fitness for Duty

Figure 1:
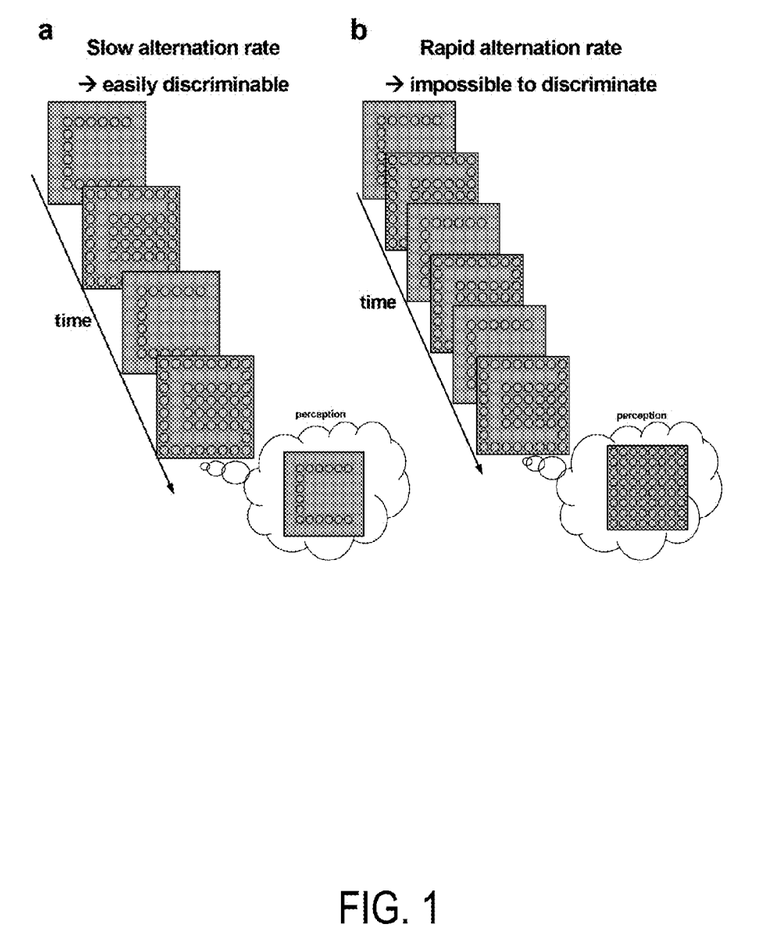
FIG. 1 illustrates two representations of an alternating display on a single LED array, in accordance with embodiments of the invention. Letters are alternated rapidly with their negatives on the LED arrays. (a) At slow rates (e.g., period=50 milliseconds), a letter is easily identified. (b) At faster rates (e.g., period=20 milliseconds), the LED array appears as though all the lights are constantly on, and the letter is not identifiable.
Figure 2:
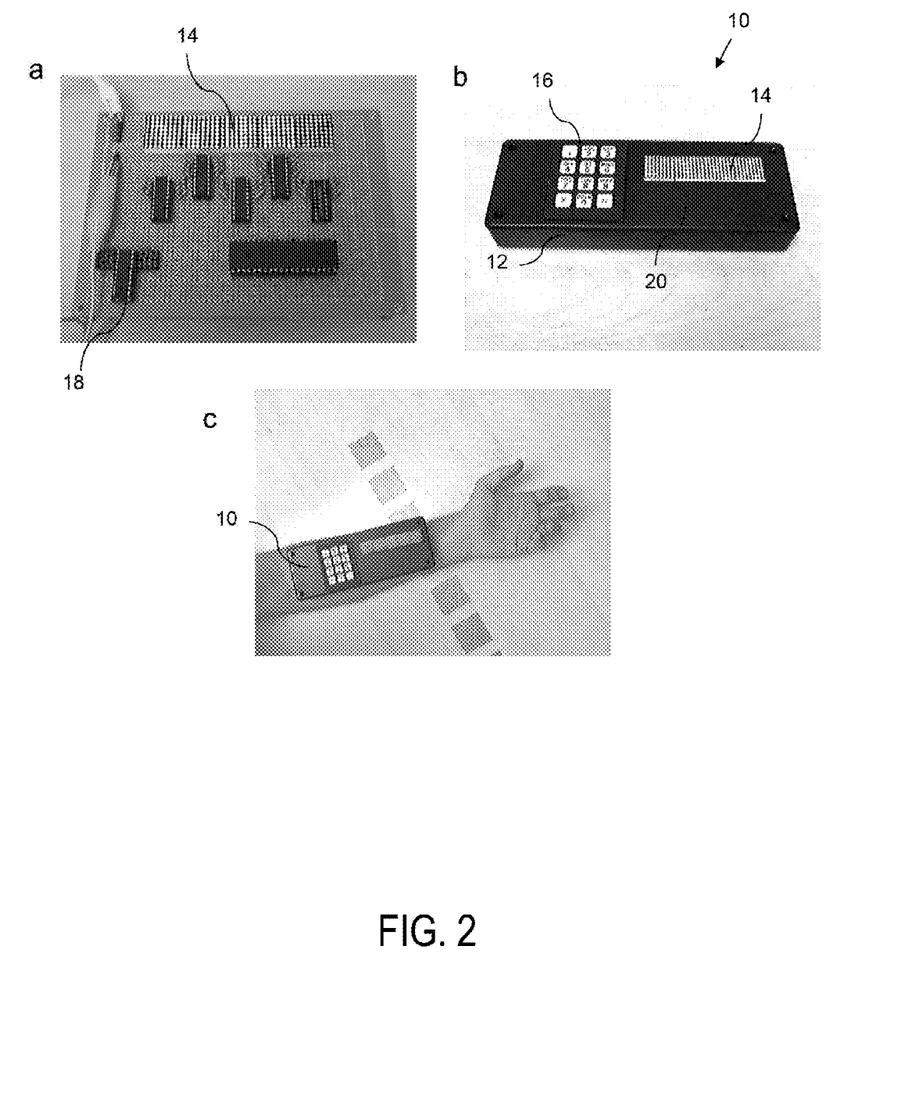
FIG. 2 is a group of photographs illustrating embodiments of the invention. Panel a: illustrates electronic circuitry and a group of LED arrays. Panel b: a portable perceptual chronometer with LED arrays and keypad. Panel c: the device of panel b shown in comparison to human arm.

As illustrated in FIGS. 1 and 2, and described below in more detail, a temporal chronometer is employed in which letters are alternated rapidly with their negatives on our LED arrays. FIG. 1a conceptually illustrates a slow alternation rate for a single LED array (e.g. period=50 milliseconds), at which a letter is typically easily identified. FIG. 1(b) conceptually illustrates a more rapid alternation rate. At faster rates (e.g., period=20 milliseconds), the LED array appears as though all the lights are constantly on, and the letter is not identifiable. After the device is turned on, subjects watch a briefly presented (e.g., 1.5 seconds), rapidly alternating sequence of letters or numbers on the LED array, illustrated in FIG. 2. They then report onto the attached keypad the sequence they perceived. Depending on the speed of information uptake of the viewer (which is determined by his or her window of integration), the word will either be identifiable or will look like a blank screen. It is proposed that in conditions of fatigue the temporal window of integration expands, causing the threshold between these states to change. The perceptual chronometer presents a character string, preferably a letter and/or number string of 1 to 5 or more characters, more preferably a 4 or 5-character word or number string, to subjects at different alternation rates and asks them to report what they saw. A subject whose test threshold has deviated significantly (i.e., increased threshold) from his baseline threshold is judged to be fatigued. For example, a subject presented with a letter and its negative at a slow rate of alternation, as in FIG. 1, panel a, has no trouble identifying the letter. But as the rate of alternation increases, a threshold is reached where the information is presented too rapidly, and the image (e.g., letter or number) can no longer be discriminated from a uniform display (FIG. 1. panel b). In the latter case, the letter and its negative will perceptually overlap as though they were presented simultaneously. The alternation rate at which a letter becomes unreadable varies by individual. The window of integration changes in conditions of fatigue. That is, with extreme fatigue, for example, the visual system takes a longer time to piece together its view of what is happening in the outside world. As a result, alternating stimuli can perceptually overlap even when they are presented at slower rates than normal. Thus, by measuring an individual's baseline threshold, and then measuring again in conditions of fatigue, it is determined if the individual's baseline has changed sufficiently to warrant relief from duty.

Figure 3:
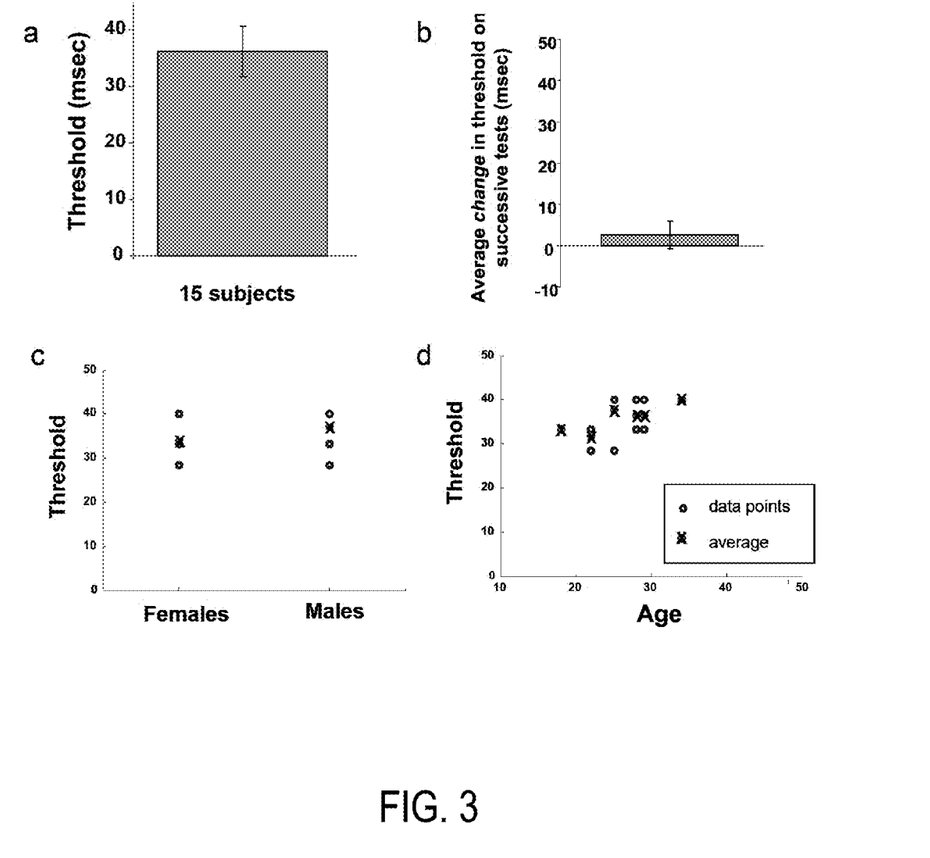
FIG. 3 shows the results of preliminary tests. Panel a shows the average threshold for the 15 subjects lies within a narrow range. Panel b shows that the thresholds are stable over different times of day, as shown by the 2.6 msec average change in threshold upon successive testing. Panel c is a graph of threshold vs. gender, showing that there is no clear gender difference in thresholds. Panel d is a graph of threshold vs. age, in which there appears to be a slight trend for older subjects to have higher thresholds.

A set of initial baseline threshold data is shown in FIG. 3. The variance across subjects' threshold was small, all thresholds being between 28 msec and 40 msec, with a mean of 36 msec (FIG. 3, panel a). Subjects' thresholds are fairly stable over repeated testings at different times of day (changes of only 2.6 msec between sessions; FIG. 3, panel b). Additionally, there is no obvious threshold difference between genders (FIG. 3, panel c). There may be a slight trend with age, wherein older subjects require slower presentations to be able to read the words (FIG. 3, panel d). Although the foregoing discussion focuses primarily on fatigue conditions, it is believed that there may be threshold changes in conditions of sleep deprivation, alcohol use, drug use, hypoxia, high adrenaline conditions, and other conditions, which will also be reflected in similar threshold screening tests. The results reported with respect to fatigue are considered representative of the results that will be obtained under other conditions of impairment of an individual when performing the above-described visual task. Performance on the visual task will also be correlated with independent physiological markers as well as task performance.

Preferably, each individual is measured for his or her personal baseline threshold. However, the initial baseline threshold data presented in FIG. 3 confirms that the perceptual speed of information intake lies in a fairly narrow, stable range for subjects at rest. Accordingly, in some testing situations it may be preferred to perform threshold screening on an individual without first establishing a personal baseline threshold. In that case, a predetermined average threshold is used instead for comparison to obtain an estimated level of threshold change, as a measure of impairment, or lack thereof, in the individual. For instance, automobile drivers may be initially screened for alcohol impairment by comparing their test threshold levels to a predetermined baseline threshold (such as an average or median threshold of a peer group of control subjects that has been previously correlated with a maximum permissible blood alcohol level for a like group). On the basis of a predetermined excessive threshold test result a suspected drunk driver could be taken off the road. A follow-up personal baseline threshold level may be obtained on a screened individual at a later time to obtain confirmation of the test result, or to obtain a more precise comparison against the test threshold value.

A perceptual chronometer may be used in combination with a door lock, such as an airline pilots' security entrance at an airport, as another example. A pilot who demonstrates an unacceptably high threshold level will be unable to correctly key in a number and/or letter code on the attached keypad that would cause the door to unlock. Still another situation where the perceptual chronometer and testing method may be advantageously employed is in combination with a truck's ignition system, for instance. A driver who is unable to perform the visual task would be unable to start the truck's engine.

Another application for a perceptual chronometer and testing method is for mental competency screening, as an aid to documenting informed consent by an individual to a medical treatment or surgical procedure, for instance.

Not only can a perceptual chronometer and testing method measure whether an individual's perceptual clock slows during fatigue, they can also be used to determine whether perceptual clocks run faster during high stress situations in the individual tested. If so, the device may be employed in combination with other instruments or devices to advantageously present visual information more rapidly to operators on the job in high-adrenaline situations.

In many situations the test performance could be monitored by a supervisor who would receive an electronic report from the device, or the device could send out another kind of alert, such as an audible beep or a visual indication such as a light on the device, or a reading on the LED display.

The ability to rapidly assess FFD, by rapid visual measures to detect excessive fatigue and deterioration of performance, is a valuable asset in high stakes decision making in many professions, including pilots, surgeons, commercial drivers and persons in military combat situations.

Perceptual Chronometer

A device that can present letters/numbers and their negatives in order to measure an individual's windows of integration has been constructed. FIG. 2, panels a-c, illustrate a preferred portable design of a temporal chronometer. Panel a is a view showing the electronic circuitry 18 of one embodiment of the device 10. Several LED arrays deliver a rapidly alternating sequence of numbers (or letters) to the viewer. Panel b illustrates an embodiment of a completed portable device 10 with case 12, display 14 and keypad 16. Subjects enter the perceived sequence into the attached keypad 16. The onboard microchips randomize the sequences and analyze the keypad input to make an immediate fitness for duty determination. Panel c of FIG. 2 shows the size of an embodiment of the device in comparison to human arm. It is configured for being strapped onto the subject, if desired, for testing under fast paced, high optempo situations.

The chronometer 10 comprises a display 14 of several LED arrays driven by multiple programmable microchips, with an attached keypad 16. The device is programmed such that letters can be alternated rapidly with their negatives on the LED arrays, also shown in FIG. 1, panels a and b. As illustrated in panel a, at slow rates (e.g., period=50 milliseconds), a letter is easily identified. As illustrated in panel b, at faster rates (e.g., period=20 milliseconds), the LED array appears as though all the lights are constantly on, and the letter is not identifiable. Accordingly, subjects watch a briefly presented, rapidly alternating sequence of images (e.g. letters, numbers) on the LED arrays (FIG. 2, panels b and c). They then report onto the attached keypad the sequence they perceived. Depending on the speed of information uptake of the viewer (which is determined by the viewer's window of integration), the images will either be identifiable or will look like a blank screen.

Figures 4, 4A:
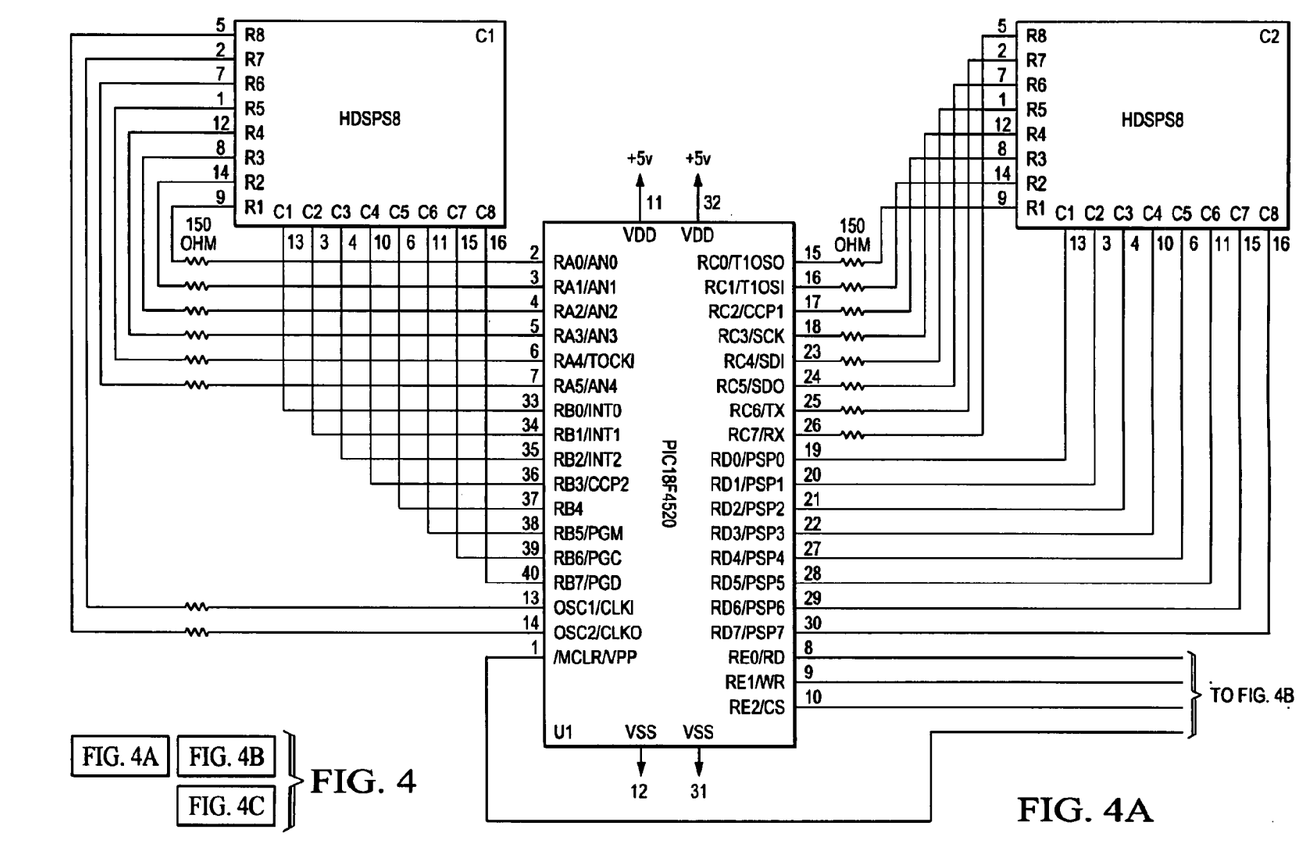
FIG. 4 illustrates circuitry that is housed within the chronometer device of FIG. 2, in accordance with an embodiment of the invention. The circuitry collects signals from a user-activated keypad and compares the signals with those corresponding to a plurality of images shown on the LED arrays of FIG. 2 to determine the mental condition of a user or test subject).
Figure 4B:
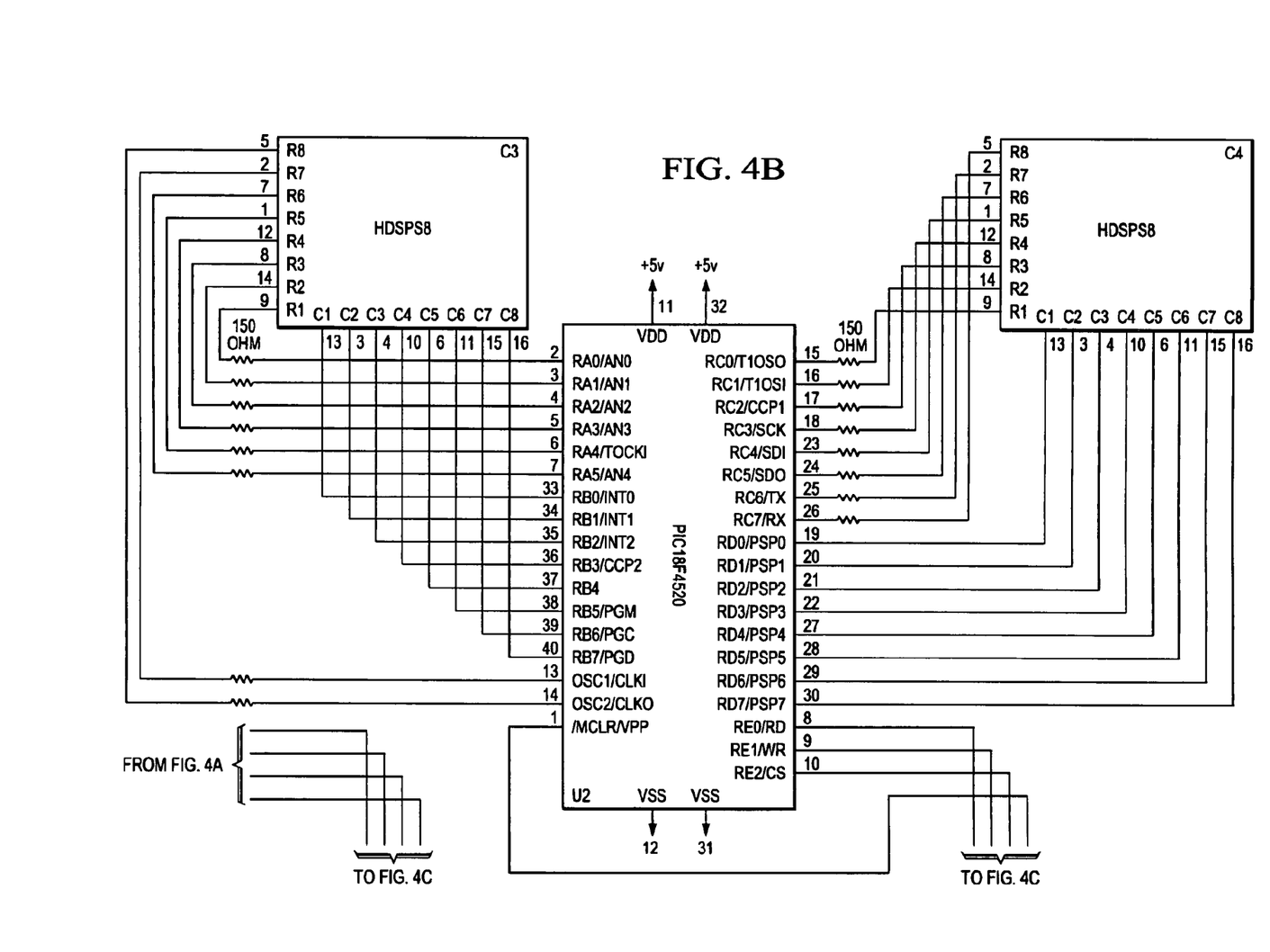
Figure 4C:
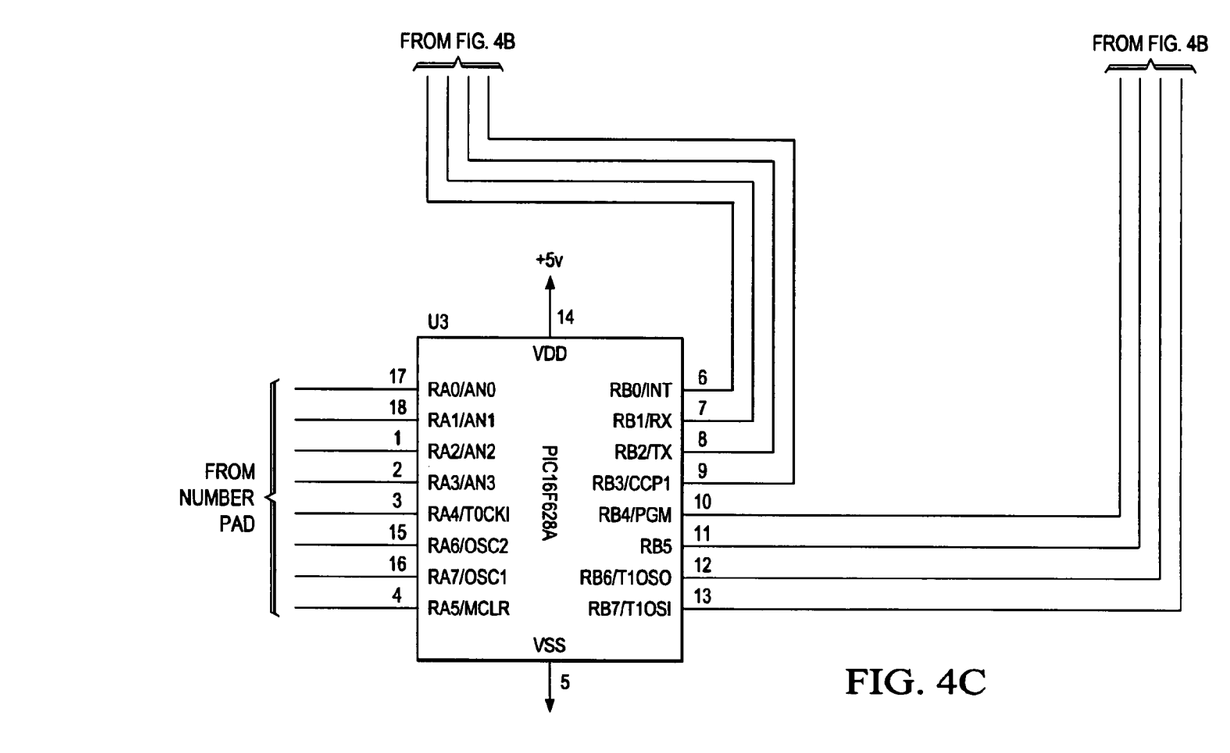

As shown in panel b of FIG. 2, an embodiment of the device comprises a chassis or case 10 having a keypad 16 and an LED array 14 on a user-accessible surface 20. The chassis may be configured for being hand held, or it may be adapted for being worn on any desired location on the human body, as illustrated in FIG. 2, panel c. The keypad and the LED array are electrically coupled to circuitry housed inside the chassis. FIG. 4 shows an exemplary circuit diagram. In some embodiments, the circuitry comprises a plurality of PICs, a plurality of LED arrays (e.g., 8×8 LED arrays), and other circuitry (e.g., wiring, resistors) coupled therebetween. In a preferred embodiment, the PIC16F628A is a master to slave PICs PIC18F4520. Both types of PICs (PIC16F628A and PIC18F4520) are available from Microchip Corp. The blocks marked "HDSPS8" are 8×8 LED arrays available from Agilent Technologies. The circuitry shown in FIG. 4 is not exhaustive, and although not specifically shown, may further comprise scanning circuitry to monitor user input provided to the keypad and to transfer electronic signals from the keypad to the circuitry shown in FIG. 4.

As shown, each PIC18F4520 PIC is coupled to two 8×8 LED arrays, although the scope of disclosure is not limited as such. An 8×8 LED array comprises 8 rows and 8 columns of diodes which are electrically activated or deactivated such that the LED array produces a single image. Each LED array preferably receives a total of 16 electrical signals from a corresponding PIC18F4520. More specifically, 8 of these 16 signals are coupled to the rows of the 8×8 LED array and the remaining 8 signals are coupled to the columns of the 8×8 LED array, as shown. In embodiments where the LED array is larger or smaller than 8×8, a greater or fewer number of signals may be provided to the array. The signals cause the LED array to display a particular image (e.g., a number, a letter). The signals also indicate to the LED array the alternation rate at which the images and their negatives are to be displayed. The slave PICs PIC18F4520 are provided with the appropriate image and alternation rate information by the master PIC16F628A, as described further below.

In operation, a user presses a key or sequence of keys on the keypad to initialize testing. In some embodiments, the user may use the keypad to enter a user-specific PIN which causes the PIC16F628A to load the user's personal baseline alternation rate (e.g., the maximum alternation rate at which the user can still identify the images on the LED arrays while rested and sober). In either case, when activated by a user, the keypad sends signals to the PIC16F628A. In turn, the PIC16F628A generates data signals that indicate to the LED arrays the images that are to be displayed on the arrays, as well as the alternation rate that is to be used. For example, the PIC16F628A may "recognize" a user based on the PIN entered by the user. The PIC16F628A may further retrieve the user's personal baseline alternation rate (e.g., stored in memory) and may send the alternation rate, along with the appropriate image(s), to the PICs PIC18F4520 using electrical signals. The PICs PIC18F4520 then may use the image and alternation rate information to generate and alternate the appropriate images on the LED arrays. If sober and well rested, the user will be able to determine the image being displayed, and will be able to enter a sequence on the keypad that corresponds with the image.

For example, the LED arrays flash a number sequence "6-2-5-0" at the user's baseline alternation rate. If the user is sober and rested, the user perceives that the number sequence being displayed is "6-2-5-0" and enters that number sequence using the keypad, thus passing the test. A passing result may be indicated by, for example, a green LED located on an outer surface of the chronometer chassis. If the user is not sober and/or rested, the user is not able to determine the number sequence being displayed, and because the user cannot enter the correct number sequence on the keypad, the user fails the test. A failing result may be indicated by, for instance, a red LED located on an outer surface of the chronometer chassis.

In some embodiments, the user may be given additional opportunities to correctly determine the number sequence being displayed, albeit at a lower alternation rate. The user may be given additional opportunities until the user is able to correctly determine the number sequence being displayed. Each time the user is given another opportunity, the alternation rate of the images is lowered. When the user enters the correct number sequence on the keypad, the PIC16F628A may record the current alternation rate and further compare this alternation rate to the user's baseline alternation rate. In this way, the device determines if the user demonstrates a sufficiently large shift from baseline to qualify him as unfit for duty. This measure enjoys the advantage of objectivity, allowing a subject to be temporarily dismissed from duty without favoritism or prejudice.

The concept of providing the user with additional opportunities may be implemented more broadly using an "adaptive staircase" algorithm. The adaptive staircase algorithm zooms in quickly on an individual user's threshold. Specifically, the first alternation rate is slow, at a rate that users should have no trouble reading. The next trial is very rapid, at a rate that users are typically unable to read. After this, when the algorithm detects that a user got a correct answer, it presents the next trial at a faster alternation rate. Conversely, when the user gets an incorrect answer, the algorithm presents the next trial at a slightly slower rate. With this method, the algorithm quickly zooms in on the user's threshold. A user must get 3 out of 5 trials correct at a given alternation rate, and 3 out of 5 wrong at the next fastest rate, to achieve a final score. Embodiments of the testing method need no setup or calibration and yield a rapid assessment in about 60 seconds or less. In some embodiments, the perceptual chronometer also includes an indicator on the device which is activated if the perceived sequence entered by the user does not match a specified displayed sequence. For instance, an unsuccessful test result may be indicated by a red blinking light that is visible on an outer surface of the device, or an audible tone may sound. Alternatively, or additionally, the device may be configured with an indicator that is activated if the perceived sequence which is entered by the uses matches the displayed sequence. For example, a successful test result may be indicated by a green light on the device and/or a different audible tone. In some embodiments, the device also includes an eye tracker that measures the extent of eye movement of the subject during a trial. The trials in which the subject blinked or made large eye movements may then be excluded.

In some situations the adaptive staircase algorithm may determine that the user's threshold is above the user's baseline rate. This scenario may arise in high-adrenaline situations, such as while flying a fighter jet plane in combat. In such situations, the user's increased threshold may be used advantageously. For example, if it is determined that the fighter jet pilot's threshold is above the baseline rate, then the rate at which the fighter jet's instrumentation panels display information may be accelerated, thus taking advantage of the pilot's faster threshold.

As an alternative to a portable perceptual chronometer as described above, in some embodiments a computerized version, appropriately programmed, is provided for displaying on a computer screen. Preliminary data was collected with the computerized system by having observers sit comfortably in front of the computer, upon which the computerized version was programmed using MATLAB 7.0 on a Dell computer with a 19" CRT monitor. In accordance with the programming, a graphical replica of 4 LED arrays appears on a blank screen for 1.5 seconds, during which time the numbers alternate rapidly. On any given trial, the numbers alternate at a fixed rate; this rate varies from trial to trial. Users watch the strip of numbers, and then enter the numbers that they perceived into the computer's keypad. They do not receive feedback, and they are under no time pressure to complete the test. The results of these preliminary tests are described above and shown in FIG. 3.

Figure 6:
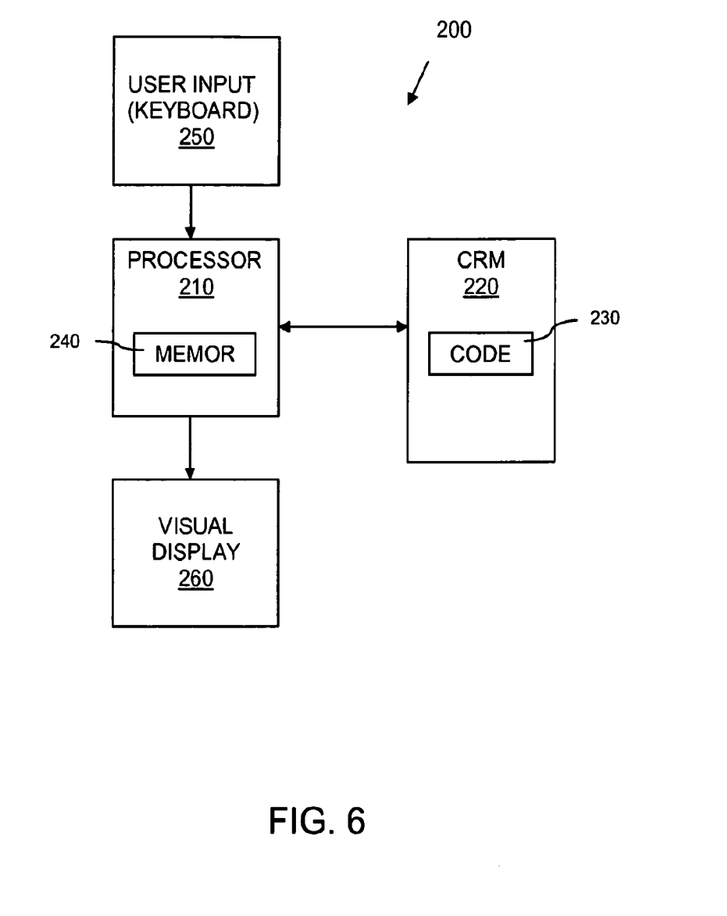
FIG. 6 is a schematic box diagram showing computer readable medium usable in an embodiment of a device for measuring the speed of visual perception.

FIG. 6 shows an illustrative embodiment of a visual perception measurement device 200. As shown in FIG. 6, device 200 comprises a processor 210 coupled to a computer-readable medium (CRM) 220, a visual display 260, input device 250. The CRM 220 comprises any suitable type of volatile memory (e.g., random access memory), non-volatile memory (e.g., hard disk drive, flash memory, read-only memory, compact disk read-only memory, etc.), or combinations thereof. The CRM 220 stores code 230 that is executable by processor 210. The processor 210 may include memory 240. Likewise, the CPM 220 may be part of, or separate from, processor 210. In at least some embodiments, the processor 210, executing code 220, comprises logic that causes the device 200 to perform some or all of the functionality described herein attributable to the device (e.g., a perceptual chronometer or temporal eye chart).

Example 2

Temporal Eye Chart

Another embodiment of a temporal measurement device is a temporal eye chart (TEC). By making the test instantaneous, inexpensive, free of the need of specialized training and not susceptible to false positive outcomes, testing of the brain is now made more accessible than before. In preferred embodiments, the TEC is a quick and easy method for measuring the speed of information processing in the brain. It potentially provides a reliable and sensitive measure of processing speed that is free from educational and cultural bias. Because it can be read in a manner analogous to a traditional wall eye chart used for testing vision, the TEC is simple for a physician to implement, does not suffer from practice effects, and can be easily applied in community healthcare settings.

A temporal eye chart (TEC) device and the associated algorithm that together yield a rapid measure of changes from the normal speed of perception are described in this example, along with an automated method for measuring the speed of human visual perception. Potential areas of application for this device include, but are not limited to, psychopharmacology, early disease diagnosis and operator changes due to fatigue, excessive stress, alcohol or drugs.

Figure 5:
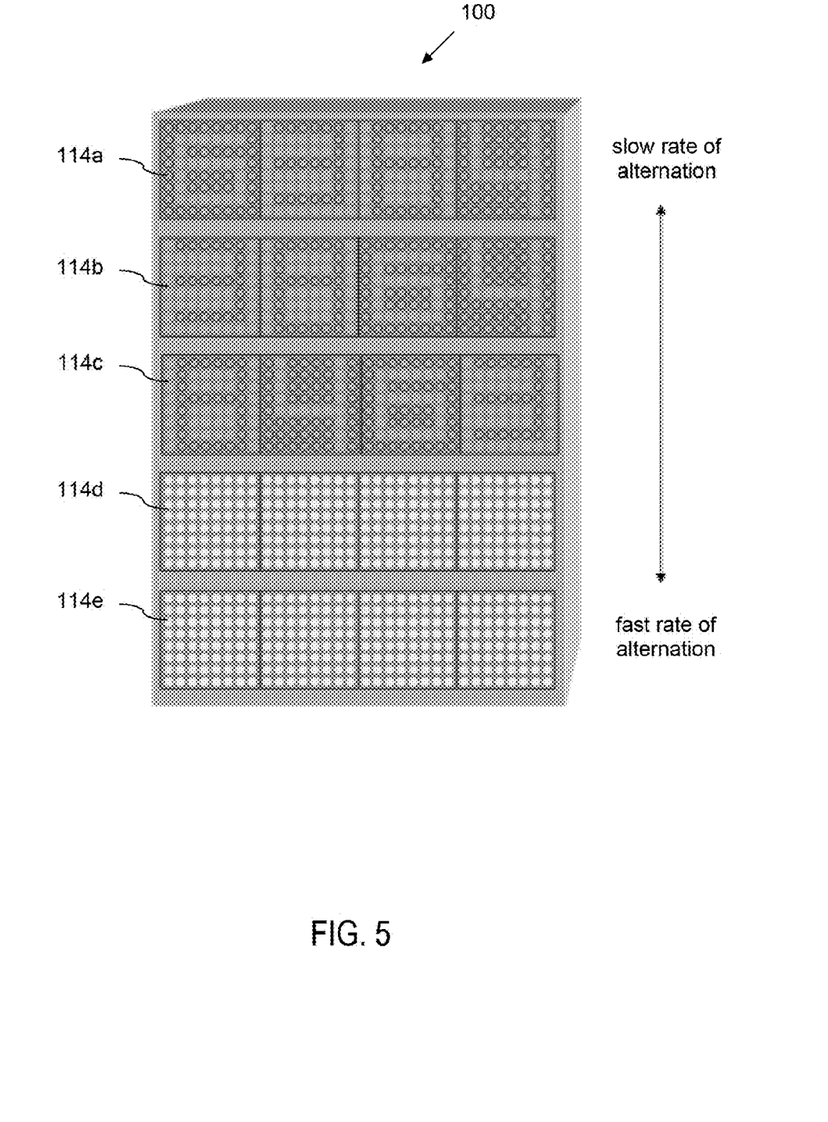
FIG. 5 illustrates an embodiment of a temporal eye chart in accordance with an embodiment of the invention. The chart contains a stacked series of five groups of four LED arrays for displaying five 4-character sequences, at increasing rates of alternation of positive and negative images from top to bottom of the stack.

In one embodiment, illustrated in FIG. 5, a device 100 is shown which is configured to present letters and/or numbers, and their negatives, in order to measure an individual's unique windows of integration. Device 100 comprises a display of several rows of LED arrays 114a-e driven by a programmable microchip and electronic circuitry which may be similar to that described above in Example 1 and illustrated in FIG. 4. The device may be equipped with a reset button (not shown), for resetting the sequences on the display. Subjects watch a briefly presented, rapidly alternating sequence of letters or numbers on the rows of LED arrays. Each row has a different alternation frequency. For example, as illustrated in FIG. 5, rows at the top (114a-c) are alternating slowly enough to be easily read, while rows at the bottom (114d-e) are alternating at a frequency too high to be read. A test subject simply reports the numbers that he or she can read. For instance, the subject might respond that "The first row reads 6-3-8-4, the second row reads 3-8-6-4, the third row reads 8-4-6-3, and I can't read anything past that." How many rows a subject can read is determined by the speed of information uptake of that particular viewer. Thus, the rows will either be identifiable to the viewer or will look like a flat screen of lights. In this way, the individual's threshold is immediately determined. Simply by looking at the TEC, the subject can report how many rows he or she is able to read. In some embodiments, the device is configured such that each time the reset button is pressed, the TEC displays randomly generated character strings or "words" (made of letters or numbers, or a combination of numbers and letters) on the rows.

In some embodiments, the individual's threshold value is compared to the same individual's threshold value from a prior TEC measurement, as a way of determining whether any changes have occurred, and the extent of any such changes. In some embodiments, the individual's threshold value is compared to a normal or standard threshold range. For some applications, the individual's threshold value is correlatable with an aspect of CNS function in the individual.

It can be readily appreciated sequence recognition is virtually impossible to fake in this perception test. If a stimulus is alternating at a rate above the patient's processing speed, it cannot be seen. This speed and ease of determining a threshold opens up the important measure of temporal processing to all patients. The TEC is not influenced by cultural factors and it has been shown to be both a valid and reliable measure of central nervous system function. It provides an objective and quantitative measure and is free of many of the methodological problems associated with rating scales. Still other potential benefits or advantages of a TEC are that it provides a mechanism for standardized and instantaneous measurement. In many applications, a TEC will be preferable over traditional methods of measuring CFFT because it yields data instantly and requires no specialized training. Further, it is virtually impossible for a test subject to falsify the outcome of a TEC test. This is because, if a stimulus is alternating above one's speed of perception, it simply cannot be reported.

In certain embodiments, a temporal eye chart is used as an aid in diagnosing Alzheimer's disease and offers potential advantages over conventional CFFT methodologies. Unlike some existing CFFT testing methods, which typically take about 15 minutes to administer, a TEC test is potentially much quicker to administer and less inexpensive. Embodiments of the TEC may be used easily in community based settings with little or no training. By implementing TEC methods, physicians will be able to begin appropriate pharmacotherapies early in the disease process, thus potentially saving neurons before extensive cognitive decline occurs and becomes clearly recognizable. In addition to offering a potentially rapid method for early diagnosis, the temporal eye chart also offers a way to advance research on the relationship between Alzheimer's disease and temporal measures.

In contrast to these existing, time consuming methods, which require time and expertise, the temporal eye chart requires no expertise to use, allows data to be collected instantaneously, and cannot be readily circumvented by the test subject.

REFERENCES

1. Eagleman, D. M. (2001) Visual Illusions and Neurobiology. *Nature Reviews Neuroscience.* 2 (12): 920-6.
2. Eagleman, D. M. & Sejnowski, T. J. (2000) Motion integration and postdiction in visual awareness. *Science.* 287 (5460): 2036-8.
3. M.-C. Rigaud and C. Flynn, Fitness for duty (FFD) evaluation in industrial and military workers, *Psychiatric Annals* 25 (4) (April 1995), 246-250.
4. "Alertness Monitoring Devices Emerge From San Diego." *Neurotech Business Report.* http://www.neurotechreports.com/pages/alertness.html.
5. Caldwell J A, Prazinko B, Caldwell J L. Body posture affects electroencephalographic activity and psychomotor vigilance task performance in sleep-deprived subjects. *Clinical Neurophysiology.* 2003 January; 114 (1): 23-31.
6. Ocular measures of fatigue and extended wakefulness. *J Aviation, Space, Environmental Medicine*, Vol 76, No 3.
7. Di Lollo V. Temporal integration in visual memory. *J Exp Psychol Gen.* 1980 March; 109 (1):75-97.
8. Agurell, S., Levander, S. E., Binder, M. and Bader-Bartfai, A. (1976). Pharmacokinetics of D-tetra-hydrocannabinol in man after smoking: relations to physiological and psychological effects. In Pharmacology of Marihuana, Brant, M. C. and Szara, T. S. (Eds), Raven Press, New York.
9. Alpern, M. and Sugiyama, S. (1961). Photic driving of the Critical Flicker Frequency. Journal of the Optical Society of America, 51, 1379-1385.
10. Apkarian, P. (1993). Temporal frequency responsivity shows multiple maturational phases: state-dependent visual evoked potential luminance flicker fusion from birth to 9 months. Visual Neuroscience, 10, 1007-1018.
11. Berlin, I., Warot, D., Hergueta, T., Molinier, P., Bagot, C. and Puech, A. J. (1993). Comparison of the effects of zolpidem and triazolam on memory functions, psychomotor performances, and postural sway in healthy subjects. Journal of Clinical Psychopharmacology, 13, 100-106.
12. Curran S. & Wattis J. Critical Flicker Fusion Threshold: A Potential Useful Measure for the early Detection of AD. Human Psychopharmacology Clinical And Experimental 2000; 15:103-112.
13. Danjou, P., Warot, D., Hergueta, T., Lacomblez, L., Bouhours, P. and Puech, A. J. (1992). Comparative study of the psychomotor and antistress effects of ritanserin, alprazolam and diazepam in healthy subjects: some trait anxiety-independent responses. International Clinical Psychopharmacology, 7 (2), 73-79.
14. Dember, W. N. and Warm, J. S. (1979). Psychology of Perception, 2nd Edn. Holt, Rinehart and Winston, New York, pp. 20-54.
15. Evans, B. J., Drasdo, N. and Richards, I. L. (1994). An investigation of some sensory and refractive factors in dyslexia. Vision Research, 34, 1913-1926.
16. Gatti, G., Barzaghi, N., Dominijanni, R., Cordaro, C. and Perucca, E. (1993). Enantioselective effects of levodropropizine and dropropizine on psychomotor functions in normal volunteers: a placebo-controlled, double-blind comparative study. Drugs Under Experimental & Clinical Research, 19, 33-39.
17. Gerrard, L., Wheeldon, N. M. and McDevitt, D. G. (1993). Central effects of combined bendrofluazide and atenolol administration. A single dose study in normal subjects. European Journal of Clinical Pharmacology, 45, 539-543.
18. Ginsburg, N. (1967). Ascending-descending differences in CFF measurement as a function of eccentricity and starting point. Journal of Psychology, 67, 161-167.
19. Gortelmeyer, R. and Wiemann, H. (1982). Retest reliability and construct validity of critical flicker fusion frequency. Pharmacopsychiatria, 15 (Suppl. 1), 24-28.
20. Gortelmeyer, R. and Zimmermann, P. (1982). Neurophysiological determinants of the critical flicker fusion frequency (CFF). In Flicker Techniques in Psychopharmacology, Ott, H. and Kranda, K. (Eds), Beltz, Weinheim, pp. 23-38.
21. Grunberger, J., Saletu, B., Berner, P. and Stohr, H. (1982). CFF and assessment of pharmacodynamics: role and relationship to psychometric, EEG and pharmacokinetic variables. Pharmacopsychiatria, 15, (Suppl. 1), 29-35.

22. Grundstrom, R., Holmberg, G., Ledermann, H. and Livstedt, B. (1977). Sedative properties of doxepin in comparison with diazepam. Psychopharmacology, 54, 165-169.
23. Grundstrom, R., Holmberg, G. and Hansen, T. (1978). Degree of sedation obtained with various doses of diazepam and nitrazepam. Acta Pharmacologica Toxicologica, 43, 13-18.
24. Hale, A. S. and Pinninti, N. R. (1995). Critical flicker fusion threshold and anticholinergic effects of chronic antidepressant treatment in remitted depressives. Journal of Psychopharmacology, 9, 258-266.
25. Hill, A. J., Hindmarch, I. and Walsh, R. D. (1981). Tolerability of nocturnal doses of clobazam in anxious patients in general practice. In Clobazam, Hindmarch, I. and Stonier, P. D. (Eds), The Royal Society of Medicine International Congress and Symposium Series No. 43, Academic Press, London, pp. 133-140.
26. Hindmarch, I. (1982). Critical flicker fusion frequency (CFF): the effects of psychotropic compounds. Pharmacopsychiatria, 15 (Suppl. 1), 44-48.
27. Hindmarch, I. (1987b). Antidepressant drugs and cognitive function. In Diagnosis and Treatment of Depression, Biziere, K., Garattini, S. and Simon, P. (Eds), Medsi/McGraw, Paris, pp. 356-365.
28. Hindmarch, I., Kerr, J. S. and Sherwood, N. (1991). The effects of alcohol and other drugs on psychomotor performance and cognitive function. Alcohol & Alcoholism, 26, 71-79.
29. Hindmarch, I. and Wattis, J. P. (1988). Measuring effects of psychotropic drugs. In Psychological Assessment of the Elderly, Wattis, J. P. and Hindmarch, I. (Eds), Churchill Livingstone, Edinburgh, pp. 180-197.
30. Hindmarch, I. (1994). Instrumental assessment of psychomotor functions and the effects of psychotropic drugs. Acta Psychiatrica Scandinavica, 380, 49-52.
31. Holmberg, G. (1981). Critical flicker fusion (CFF) test for sedative effect of antidepressants. In Recent Advances in the Treatment of Depression, Carlsson, A., Gottfries, C. G., Holmberg, G., Modigh, K., Svensson, T. and Ogren, S. O. (Eds), Acta Psychiatrica Scandinavica, 63 (Suppl. 290), 289-301.
32. Holmberg, G. and William-Olsson, U. (1963). The effect of benzquinamide, in comparison with chlordiazepoxide and placebo, on performance in some psychological tests. Psychopharmacologia, 4, 402-417.
33. King, D. J., Bell, P., Bratty, J. R. and McEntegart, D. J. (1991). A preliminary study of the effects of flosequinan on psychomotor function in healthy volunteers. International Clinical Psychopharmacology, 6, 155-168.
34. Kranda, K. (1982a). Potential applications of various flicker techniques in psychopharmacology: the aims and limits. In Flicker Techniques in Psychopharmacology, Ott, H. and Kranda, K. (Eds), Beltz, Weinheim, pp. 14-22.
35. Lader, M. H. and Bruce, M. S. (1989). The human psychopharmacology of the methylxanthines. In Human Psychopharmacology: Measures and Methods, Vol. 2, Hindmarch, I. and Stonier, P. D. (Eds), John Wiley, Chichester, pp. 179-200.
36. Levander, S. E. (1982). Computerised CFF: reliability and validity of two psychophysical techniques. Pharmacopsychiatria, 15 (Suppl. 1), 21-33.
37. Misiak, H. (1967). The flicker fusion test and its applications. New York Academy of Sciences, 29, 616-622.
38. Parrott, A. C., Hindmarch, I. and Stonier, P. D. (1982). Nomifensine, Clobazam and HOE 8476: effects on aspects of psychomotor performance and cognitive ability. European Journal of Clinical Pharmacology, 23, 309-313.
39. Parrott, A. C. (1982b). The effects of clobazam upon Critical Flicker Fusion Thresholds: a review. Drug Development Research (Suppl.), 1, 57-66.
40. Parrott, A. C. and Hindmarch, I. (1975). Arousal and performance: the ubiquitous inverted U relationship. Comparison of changes in response latency and arousal level in normal subjects induced by CNS stimulants, sedatives and tranquillizers. IRCS Medical Science, Clinical Pharmacology and Therapeutics; Psychiatry and Clinical Psychology. Psychology, 3, 176.
41. Ponciano, E., Relvas, J., Mendes, F., Lameiras, A., Vaz Serra, A. and Hindmarch, I. (1981). Clinical effects and sedative activity of bromazepam and clobazam in the treatment of anxious out-patients. In Clobazam. Hindmarch, I. and Stonier, P. D. (Eds), The Royal Society of Medicine International Congress and Symposium Series No. 43, Academic Press, London, pp. 125-131.
42. Porter, L. (1986). Age, personality and circadian effects on critical flicker fusion thresholds. Ph.D. thesis. University of Leeds.
43. Sherwood, N. and Hindmarch, I. (1993). A comparison of five commonly prescribed antidepressants with particular reference to their behavioural toxicity. Human Psychopharmacology, 8, 417-422.
44. Siegfried, K., Jansen, W. and Pahnke, K. (1984). Cognitive dysfunction in depression. Drug Development Research, 4, 533-553.
45. Siegfried, K. and O'Connolly, M. (1986). Cognitive and psychomotor effects of different antidepressants in the treatment of old age depression. International Clinical Psychopharmacology, 1, 231-243.
46. Sherwood, N. (1994). Effects of nicotine on human psychomotor performance. Ph.D. thesis, University of Leeds.
47. Smith, J. M. and Misiak, H. (1973). The effect of iris colour on critical flicker frequency (CFF). Journal of General Psychology, 89, 91-95.
48. Simonson, E. and Brozek, J. (1952). Flicker fusion frequency: background and applications. Physiological Reviews, 32, 349-378.
49. Smith, J. M. and Misiak, H. (1976). Critical flicker frequency (CFF) and psychotropic drugs in normal human subjects: a review. Psychopharmacology, 47, 175-182.
50. Stonier, P. D. and Hindmarch, I. (1985). The effects of combining clobazam with nomifensine on psycho-motor performance in healthy subjects: a brief review. In Clobazam: Human Psychopharmacology and Clinical Applications, Hindmarch, I., Stonier, P. D. and Trimble, M. R. (Eds), The Royal Society of Medicine International Congress and Symposium Series No. 74, Oxford University Press, Oxford, pp. 59-68.
51. Rombaut, N. E. I. and Hindmarch, I. (1994). Psychometric aspects of antihistamines: a review. Human Psychopharmacology, 9, 157-169.
52. Turner, P. (1968). Critical flicker frequency and centrally acting drugs. British Journal of Ophthalmology, 52, 245-250.
53. Moulden, B., Renshaw, J. and Mather, G. Two channels for flicker in the human visual system. Perception. 1984; 13 (4):387-400.
54. Ali, M. R. and Amir, T. Critical flicker frequency under monocular and binocular conditions. Percept Mot Skills. 1991 April; 72 (2):383-6.
55. McNemar Q. "On the use of latin squares in psychology." Psychol Bull. 1951 September; 48 (5):398-401.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. The disclosures of all patents, patent applications and publications cited herein are hereby incorporated herein by reference to the extent that they describe materials, methods or other details supplementary to those set forth herein.

What is claimed is:

1. A device for measuring the speed of visual perception of an individual, the device comprising:
   a visual display configured to repeatedly display a time sequence of a positive alphanumeric pattern followed by a negative alphanumeric pattern at a predetermined rate, the negative alphanumeric patterns being an inverse of the positive alphanumeric patterns;
   a user input device for entering a displayed alphanumeric pattern as perceived by a user; and
   a microprocessor operatively coupled to said user input device and display, and configured to determine a threshold value of a rate at which the user cannot differentiate the repeated time sequence of the positive and negative alphanumeric patterns by comparing the entered displayed alphanumeric pattern as perceived by the user to the displayed time sequence.

2. The device of claim 1, wherein the predetermined rate is specific to a previously determined threshold of the user.

3. The device of claim 1, wherein the microprocessor causes the repeated time sequence of positive and negative alphanumeric patterns to be displayed at a rate that is determined based on a user-specific code entered by the user using the user input device.

4. The device of claim 1, wherein the microprocessor is configured to cause the repeated time sequence of positive and negative alphanumeric patterns to be displayed at a different rate if the perceived sequence entered by the user does not match the displayed repeated time sequence.

5. The device of claim 4, wherein the microprocessor is configured to cause the display to repeatedly display the time sequence of positive and negative alphanumeric patterns at different rates until the entered displayed alphanumeric pattern as perceived by the user matches the displayed repeated time sequence.

6. The device of claim 1, wherein the device is a portable device configured to be hand held or worn on the human body.

7. The device of claim 1 further comprising an indicator to indicate whether the entered displayed alphanumeric pattern as perceived by the user matches the displayed repeated time sequence.

8. The device of claim 1, wherein said microprocessor is configured to produce a report comprising said threshold value.

9. A non-transitory computer-readable medium (CRM) comprising software that, when executed by a processor, causes the processor to:
   show on a visual display a repeated time sequence of positive and negative alphanumeric patterns at a predetermined rate, the negative alphanumeric patterns being an inverse of the positive alphanumeric patterns;
   receive input from a user indicative of a displayed alphanumeric pattern as perceived by the user;
   compare said user perceived and entered alphanumeric pattern to said displayed repeated time sequence; and
   based on the comparison, determine a threshold value corresponding to the speed of visual perception of the user.

10. A system, comprising:
    control logic; and
    a user input device;
    wherein the control logic is to repeatedly cause a time sequence of positive alphanumeric patterns and corresponding negative alphanumeric patterns to be shown on a display device, to receive input from the user input device indicative of the alphanumeric pattern a user perceives to be shown on the display device, to determine the user's alternation rate based on the input from the user input device, and to determine whether the determined user's alternation rate deviates by more than a first threshold amount from a baseline alternation rate previously assessed for the user;
    wherein the negative alphanumeric patterns are an inverse of the positive alphanumeric patterns.

11. The system of claim 10 wherein the control logic is to cause the repeated time sequence of positive alphanumeric patterns and corresponding negative alphanumeric patterns to be shown on the display device at a rate that the control logic varies if the user input indicates that the user does not correctly perceive the alphanumeric patterns being shown on the display device.

12. The system of claim 11 wherein the control logic is to perform an adaptive staircase algorithm to vary the rate to thereby determine the user's alternation rate.

13. The system of claim 10 wherein the control logic comprises a microprocessor.

14. The system of claim 10 comprising an indicator to indicate whether the input received from the user input device correctly matches the repeated time sequence of positive and corresponding negative alphanumeric patterns.

15. A method, comprising:
    repeatedly causing to be displayed a time sequence of positive alphanumeric patterns followed by corresponding negative alphanumeric patterns at a rate, providing input indicative of the alphanumeric pattern a user perceives to be displayed, and varying the rate of the time sequence of positive alphanumeric patterns and corresponding negative alphanumeric patterns; and
    determining an alternation rate for the user based on a comparison of the user's input to the time sequences of positive alphanumeric patterns and corresponding negative alphanumeric patterns;
    wherein the negative alphanumeric patterns are an inverse of the positive alphanumeric patterns.

16. The method of claim 15 wherein performing the repeated display and determination of the alternation rate for the user is performed to establish a baseline alternation rate for the user.

17. The method of claim 16 further comprising:
    again performing the iteration and determination of the alternation rate for the user after establishing the baseline alternation rate to establish a second alternation rate; and
    comparing the second alteration rate to the user's baseline alternation rate.

18. The method of claim 17 further comprising determining whether the second alternation rate differs by more than a threshold amount from the user's baseline alternation rate.

* * * * *